(12) United States Patent
Hayashi et al.

(10) Patent No.: US 9,110,306 B2
(45) Date of Patent: Aug. 18, 2015

(54) TISSUE-SLICE IMAGE ACQUIREMENT AND DISPLAY APPARATUS, TISSUE-SLICE IMAGE ACQUIREMENT AND DISPLAY METHOD, AND TISSUE-SLICE IMAGE ACQUIREMENT AND DISPLAY PROGRAM

(75) Inventors: Nobuhiro Hayashi, Kanagawa (JP);
Koichiro Kishima, Kanagawa (JP);
Takashi Yamamoto, Tokyo (JP);
Nobuhiro Kihara, Kanagawa (JP);
Takamichi Yamakoshi, Tokyo (JP);
Fumiyasu Suzuki, Saitama (JP); Ryu Narusawa, Kanagawa (JP)

(73) Assignee: Sony Corporation, Tokyo (JP)

( * ) Notice: Subject to any disclaimer, the term of this patent is extended or adjusted under 35 U.S.C. 154(b) by 568 days.

(21) Appl. No.: 12/862,220

(22) Filed: Aug. 24, 2010

(65) Prior Publication Data

US 2011/0052038 A1 Mar. 3, 2011

(30) Foreign Application Priority Data

Aug. 31, 2009 (JP) ................................ P2009-200892

(51) Int. Cl.
*G06K 9/00* (2006.01)
*G02B 21/36* (2006.01)
(Continued)

(52) U.S. Cl.
CPC ............ *G02B 21/367* (2013.01); *G06K 9/3216* (2013.01); *G06K 9/3233* (2013.01); *G06T 7/0081* (2013.01); *G06T 7/0097* (2013.01); *G01N 1/312* (2013.01); *G02B 21/34* (2013.01);
(Continued)

(58) Field of Classification Search
CPC .. G06K 9/3233; G06K 9/3216; G06T 7/0081; G06T 2207/30024; G06T 7/0097; G06T 2207/10056; G01N 1/312; G02B 21/367; G02B 21/34
USPC .......................................................... 382/128
See application file for complete search history.

(56) References Cited

U.S. PATENT DOCUMENTS 7,272,252 B2 * 9/2007 De La Torre-Bueno et al. .............................. 382/133
7,826,649 B2 * 11/2010 Crandall et al. ............... 382/128
(Continued)

FOREIGN PATENT DOCUMENTS

EP 1967845 A2 1/2011
JP 2003-222801 8/2003

OTHER PUBLICATIONS

Douglas B. Murphy, Fundamentals of Light Microscopy and Electronic Imaging, Wiley-Liss, Dec. 15, 2001.*
(Continued)

*Primary Examiner* — Hiep V Nguyen
(74) *Attorney, Agent, or Firm* — K&L Gates LLP

(57) ABSTRACT

A tissue-slice image acquirement and display apparatus includes: an entire-image acquirer that acquires a bright-field image of an entirety of a first slice of a tissue and a dark-field image of an entirety of a second slice of the tissue; a modifier that modifies a profile shape of a slice portion in the dark-field image on the basis of a profile shape of a slice portion in the bright-field image; a magnified-image acquirer that determines a range encompassing the second slice on the basis of the profile shape of the modified slice portion and that acquires, in a dark field, a magnified image of the second slice in the determined range; and a display controller that causes the bright-field image to be displayed and that causes a portion of the magnified image, the portion corresponding to a position selected in the bright-field image, to be displayed.

11 Claims, 9 Drawing Sheets

(51) Int. Cl.
  *G06K 9/32* (2006.01)
  *G06T 7/00* (2006.01)
  *G01N 1/31* (2006.01)
  *G02B 21/34* (2006.01)

(52) U.S. Cl.
  CPC .............. *G06T 2207/10056* (2013.01); *G06T 2207/30024* (2013.01)

(56) References Cited

U.S. PATENT DOCUMENTS 8,391,112 B2* 3/2013 Tomita et al. ............ 369/44.32
2003/0231791 A1 12/2003 Torre-Bueno et al.
2004/0150824 A1* 8/2004 Matsumoto ................ 356/401
2007/0269085 A1 11/2007 Oshiro et al.

OTHER PUBLICATIONS

International Search Report dated Mar. 12, 2010, for European Patent Appln. No. 10008197.5.
Brown, "A Survey of Image Registration Techniques", ACM Computing Surveys, ACM, New York, NY, vol. 24, No. 4, Dec. 1, 1992, pp. 1-52.
Murphy, "Fundamentals of Light Microscopy and Electronic Imaging", Wiley-Liss, Dec. 15, 2001, p. 112.
Ogilvie, "Virtual Microscopy and Virtual Slides in Teaching, Diagnosis, and Research", CRC Press, Jun. 22, 2005, pp. 60 and 223.

* cited by examiner

TISSUE-SLICE IMAGE ACQUIREMENT AND DISPLAY APPARATUS, TISSUE-SLICE IMAGE ACQUIREMENT AND DISPLAY METHOD, AND TISSUE-SLICE IMAGE ACQUIREMENT AND DISPLAY PROGRAM

CROSS REFERENCES TO RELATED APPLICATIONS

The present application claims priority to Japanese Priority Patent Application JP 2009-200892 filed in the Japan Patent Office on Aug. 31, 2009, the entire content of which is hereby incorporated by reference.

BACKGROUND

The present application relates to a tissue-slice image acquirement and display apparatus, a tissue-slice image acquirement and display method, and a tissue-slice image acquirement and display program, which are preferably applied to, for example, the field of tissue-slice observation.

Tissue slices used in the field of pathology are fixed to glass slides and are subjected to predetermined staining. In general, when the tissue slices are stored for a long period of time, deterioration of the tissue slices, discoloration of stains applied to the tissue slices, and so on occur to thereby reduce visibility of the tissue slices under microscopes. The tissue slices may be used for diagnosis at facilities other than hospitals or the like where they were created, and are generally delivered by postal and courier services, which takes some time.

In view of such a situation, an apparatus that stores tissue slices as image data has been proposed (e.g., refer to Japanese Unexamined Patent Application Publication No. 2003-222801).

SUMMARY

In the pathology diagnosis, from the point of view of morphology, a primary determination as to the presence/absence of a malignant tumor is made using a tissue slice subjected to HE (Hematoxylin-Eosin) staining. When a malignant tumor or a malignancy-suspicious portion is found, a secondary determination as to the presence/absence of a malignant tumor, a type thereof, the degree of progression, and so on is made from the point of view of molecular biology by using a tissue slice sampled from the same tissue block as for the HE-stained tissue slice and subjected to fluorescent staining.

In the pathological diagnosis, high-definition images obtained by magnifying tissue slices by a certain magnification are used. An apparatus for obtaining high-definition magnified images captures an image of, for example, the entirety of a glass slide on which a tissue slice is placed, and a region in which the tissue slice lies is specified on the basis of the profile shape of a tissue-slice portion shown in the entirety image. The apparatus then assigns the specified region to multiple sub regions, sequentially obtains images of tissue-slice parts in the sub regions, and combines the obtained images to acquire a high-definition magnified image.

However, since a fluorescence-stained tissue slice is colorless and transparent when it is unexcited, it is difficult to locate the unexcited fluorescence-stained tissue slice on the glass slide.

Accordingly, one possible method is to capture an image of the entirety of a glass slide by exciting a fluorescence-stained tissue slice thereon and to locate the region of the tissue slice on the basis of the entirety image.

With the method, however, it is difficult to capture an image of the tissue slice with sufficient brightness since the amount of light emitted by the fluorescent stain is small, and because of an influence of disturbance such as electrical and optical noise, it is difficult to precisely extract the profile shape of a tissue-slice portion from the entirety image.

In such a case, it is difficult to precisely locate the region in which the tissue slice lies, and thus, there is a problem in that it is difficult to obtain a magnified image of the tissue slice with precision.

In a secondary pathological diagnosis, typically, a doctor, technician, or the like manually searches for, in a fluorescence-stained tissue slice, a part corresponding to a malignant tumor or a malignancy-suspicious portion in an HE-stained tissue slice. Not only is such work cumbersome for the doctor or the like, but also it takes a large amount of time.

In view of the foregoing, it is desirable to provide a tissue-slice image acquirement and display apparatus, a tissue-slice image acquirement and display method, and a tissue-slice image acquirement and display program which are can acquire magnified images with precision while enhancing convenience.

Accordingly, according to one embodiment, there is provided a tissue-slice image acquirement and display apparatus. The tissue-slice image acquirement and display apparatus includes: an entire-image acquirer that acquires a bright-field image of an entirety of a first slice of a tissue and a dark-field image of an entirety of a second slice of the tissue; a modifier that modifies a profile shape of a slice portion in the dark-field image on the basis of a profile shape of a slice portion in the bright-field image; a magnified-image acquirer that determines a range encompassing the second slice on the basis of the profile shape of the dark-field image slice portion modified by the modifier and that acquires, in a dark field, a magnified image of the second slice in the determined range; and a display controller that causes the bright-field image to be displayed and that causes a portion of the magnified image, the portion corresponding to a position selected in the bright-field image, to be displayed.

According to another embodiment, there is provided a tissue-slice image acquirement and display method. The tissue-slice image acquirement and display method includes the steps of: acquiring a bright-field image of an entirety of a first slice of a tissue and a dark-field image of an entirety of a second slice of the tissue; modifying a profile shape of a slice portion in the dark-field image on the basis of a profile shape of a slice portion in the bright-field image; determining a range encompassing the second slice on the basis of the profile shape of the dark-field image slice portion modified by the modifier and acquiring, in a dark field, a magnified image of the second slice in the determined range; and causing the bright-field image to be displayed and causing a portion of the magnified image, the portion corresponding to a position selected in the bright-field image, to be displayed.

According to yet another embodiment, there is provided a tissue-slice image acquirement and display program. The tissue-slice image acquirement and display program causes a computer to execute the steps of: acquiring a bright-field image of an entirety of a first slice of a tissue and a dark-field image of an entirety of a second slice of the tissue; modifying a profile shape of a slice portion in the dark-field image on the basis of a profile shape of a slice portion in the bright-field image; determining a range encompassing the second slice on the basis of the profile shape of the dark-field image slice portion modified by the modifier and acquiring, in a dark field, a magnified image of the second slice in the determined range; and causing the bright-field image to be displayed and causing a portion of the magnified image, the portion corresponding to a position selected in the bright-field image, to be displayed.

With this arrangement, the profile shape of the slice portion in the dark-field image is modified on the basis of the profile shape of the slice portion in the bright-field image, and the modified profile shape is used to acquire a magnified image. Thus, it is possible to precisely extract the profile shape and a magnified image of the slice portion in the dark-field image. In addition, since a bright-field image and a magnified-image portion corresponding to a position selected in the bright-field image are displayed, it is possible to enhance visibility.

According to an embodiment, the profile shape of the slice portion in the dark-field image is modified on the basis of the profile shape of the slice portion in the bright-field image, and the modified profile shape is used to acquire a magnified image. Thus, it is possible to precisely extract the profile shape and a magnified image of the slice portion in the dark-field image. In addition, since a bright-field image and a magnified-image portion corresponding to a position selected in the bright-field image are displayed, it is possible to enhance visibility. Accordingly, it is possible to provide a tissue-slice image acquirement and display apparatus, a tissue-slice image acquirement and display method, and a tissue-slice image acquirement and display program which can obtain a magnified image with high precision while improving inconvenience.

Additional features and advantages are described herein, and will be apparent from the following Detailed Description and the figures.

DETAILED DESCRIPTION

The present application will be described below in the following sequence:
1. First Embodiment, and
2. Other Embodiments.

1. Embodiment

[1-1. Configuration of Tissue-Slice Image Acquirement and Display Processing]

Figure 1:
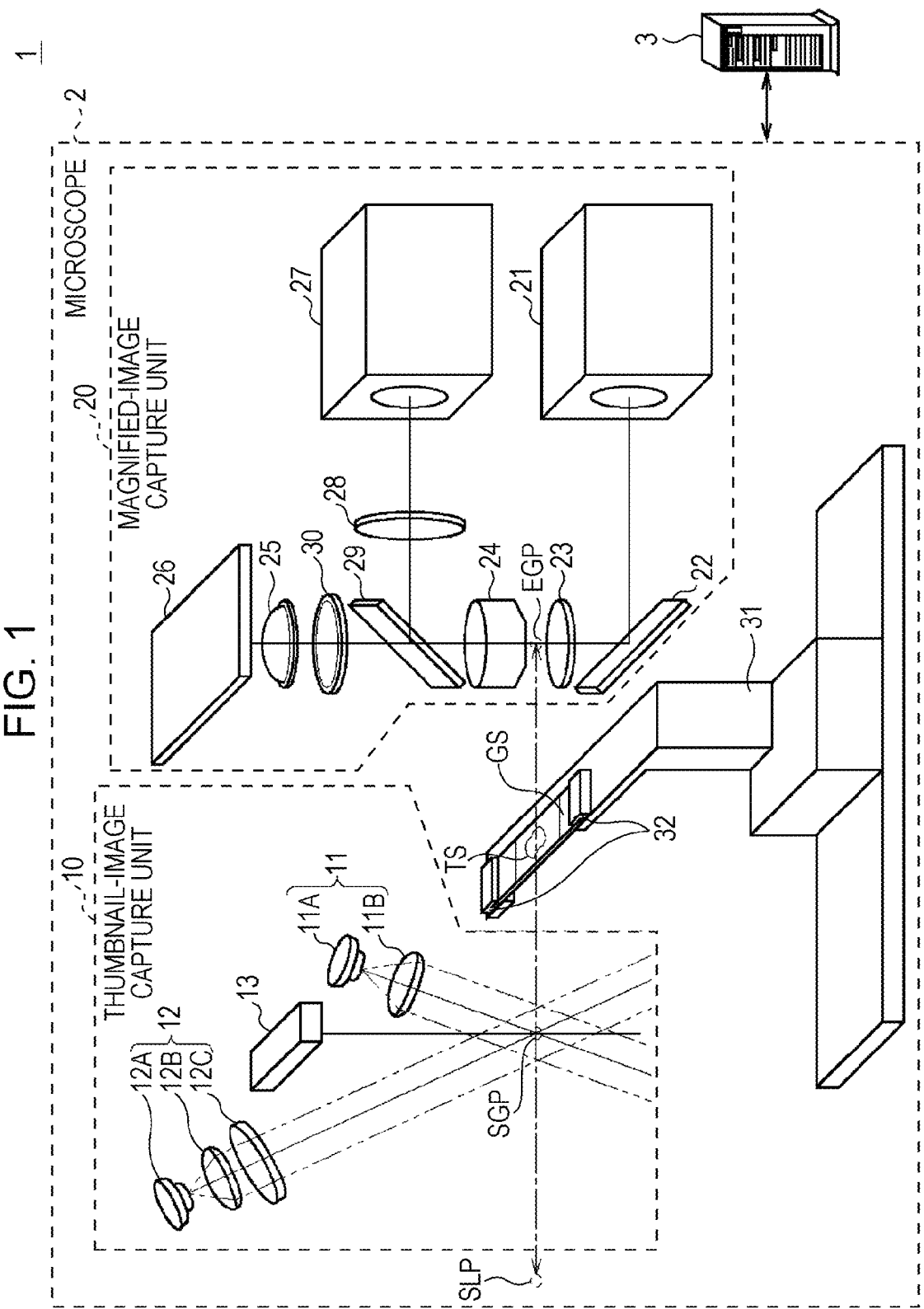
FIG. 1 is a schematic diagram showing the configuration of a tissue-slice image acquirement and display apparatus.

FIG. 1 shows a tissue-slice image acquirement and display apparatus 1 according to an embodiment. The tissue-slice image acquirement and display apparatus 1 includes a microscope 2 and a data processing unit 3.

The microscope 2 has a thumbnail-image capture unit 10 and a magnified-image capture unit 20. The thumbnail-image capture unit 10 captures an image of the entirety of a glass slide GS on which a tissue slice TS is placed. The magnified-image capture unit 20 captures a magnified image of the tissue slice TS. The microscope 2 is entirely covered with a housing (not shown) so as to prevent entry of external light thereinto.

The microscope 2 has a moveable stage 31 that can move in directions parallel and perpendicular to a plane in which the glass slide GS is placed (i.e., in xyz axis directions).

The tissue slice TS is one thinly cut from, for example, a paraffin-embedded tissue block and is fixed to the glass slide GS by a predetermined fixing method. The tissue slice TS is stained as appropriate. Examples of the staining include not only general staining, typified by an HC (Hematoxylin-Eosin) staining, MTC (Masson's trichrome) staining, IHC (immunohistochemistry) staining, Giemsa staining, Papanicolaou staining, and so on, but also fluorescent staining, such as FISH (fluorescence in-situ hybridization) and an enzyme-labeled antibody method.

A barcode (not shown) to which relevant information is recorded is attached to one end of the glass slide GS to which the tissue slice TS is fixed. Examples of the relevant information include a specimen number of the tissue slice TS, a staining method, the name, gender, and age of a person who sampled it, and the date and time of sampling.

In the microscope 2, when the glass slide GS is to be attached to or is to be removed from a slide holder 32, the moveable stage 31 moves the slide holder 32 to a glass-slide loading position SLP, located in the vicinity of an attachment/removal port (not shown), so as to allow the glass slide GS to be attached to or removed from the slide holder 32.

The thumbnail-image capture unit 10 includes a bright-field light-source system 11, a dark-field light-source system 12, and a thumbnail camera 13.

After the glass slide GS is moved to a thumbnail-image capture position SGP in conjunction with movement of the moveable stage 31, the thumbnail-image capture unit 10 captures an image of the entire glass slide GS.

More specifically, in a bright-field mode, in the thumbnail-image capture unit 10, light is emitted from a white LED (light-emitting diode) 11A in the bright-field light-source system 11 and is converted into substantially parallel light by a condenser lens 11B and the substantially parallel light is shined on the entire glass slide GS including the tissue slice TS.

When the tissue slice TS is stained by general staining, the thumbnail-image capture unit 10 forms, on an imaging plane of the thumbnail camera 13, an image of the entire glass slide GS including the tissue slice TS, the image resulting from the light.

In the bright-field mode, the data processing unit 3 drives the bright-field light-source system 11. The data processing unit 3 then uses the thumbnail camera 13 to obtain, as a bright-field thumbnail image, an image of the entire glass slide GS in a bright-field state and stores data of the bright-field thumbnail image in a predetermined data format (the data will hereinafter be referred to as "bright-field thumbnail-image data").

Figure 2:
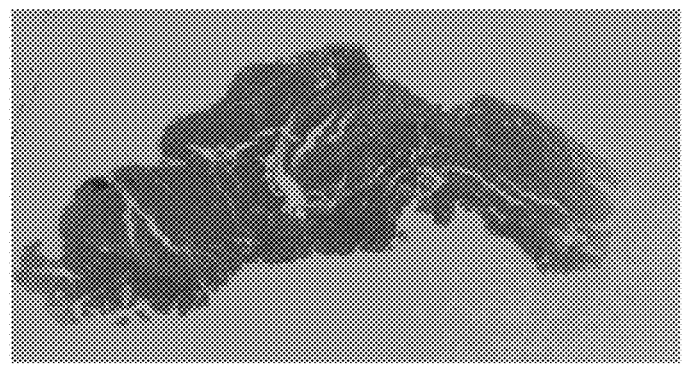
FIG. 2 is a pictorial representation of a bright-field thumbnail image.

FIG. 2 shows one example of the bright-field thumbnail image when the tissue slice TS is stained by HE staining, which is general staining. As shown, the thumbnail-image capture unit 10 can capture a bright-field thumbnail image with which the profile shape of the HE-stained tissue slice TS can be distinctly recognized.

The thumbnail-image capture unit 10 is configured so that the optical axis of light emitted from the white LED 11A is offset from the optical axis of the thumbnail camera 13 by a predetermined angle. With this arrangement, since the light emitted from the white LED 11A and reflection light resulting from reflection of the emitted light by the surface of the glass slide GS are not shined on an imaging surface of the thumbnail camera 13, the thumbnail-image capture unit 10 can prevent deterioration of the bright-field thumbnail image.

The fluorescence-stained tissue slice TS is substantially transparent in an unexcited state, and thus, when an image is captured in the bright-field mode, the tissue slice TS is not shown in the image.

One example of the fluorescent stain will now be described. To determine the presence/absence of HER-2 (Hunan Epithelial growth factor Receptor type 2) proteins in mammary gland tissue, the tissue slice TS is stained using, for example, a reagent in PathVysion® HER-2 DNA probe kit from Abbott Laboratories.

This reagent includes a probe for hybridization to the HER-2/neu gene that encodes the HER-2 proteins and a probe for hybridization to the alpha-satellite DNA sequences at the centromeric region of chromosome 17.

When the tissue slice TS is illuminated with excitation light for exciting the probes, the probes are excited to emit fluorescence. In this case, the probe for hybridization to the HER-2/neu gene and the probe for hybridization to the alpha-satellite DNA sequences emit fluorescence having wavelengths that are different from each other.

In molecular diagnosis, on the basis of the ratio of the number of HER-2/neu genes in a nucleus cell to the number of alpha-satellite DNA sequences, a determination is made as to an increase in the number of HER-2/neu genes.

Thus, in order to determine the number of HER-2/neu genes in a nucleus cell and the number of alpha-satellite DNA sequences, DAPI (4',6-diamidino-2-pheylindole), which is a reagent for staining nucleus cells is added to the PathVysion reagent to stain the tissue slice TS.

The DAPI reagent is more resistant to discoloration than the probes for hybridization to the HER-2/neu genes and the alpha-satellite DNA sequences and is excited by light with a wavelength of about 365 nm, which is different from those of the probes.

In a dark-field mode, the thumbnail-image capture unit 10 causes an ultraviolet LED 12A in the dark-field light-source system 12 to emit light with a wavelength of 365 nm (which light may hereinafter be referred to as "excitation light"). The excitation light emitted from the ultraviolet LED 12A is converted into substantially parallel light by a condenser lens 12B, the substantially parallel light is subjected to filtering by an excitation filter 12C, and the resulting light is shined on a region in which the tissue slice TS is placed.

The region in which tissue slice TS is placed is, for example, a region in which a cover glass (not shown), which, together with the glass slide GS, sandwiches the tissue slice TS on the glass slide GS.

When the tissue slice TS is stained with fluorescent stain including DAPI, the DAPI in a tissue-slice TS portion is excited by the excitation light emitted from the ultraviolet LED 12A (which serves as an excitation-light source) to thereby emit fluorescence. In this state, the thumbnail camera 13 forms, on the imaging plane, an image of the entire glass slide GS together with the fluorescent tissue-slice TS portion.

In the dark-field mode, the data processing unit 3 drives the dark-field light-source system 12. The data processing unit 3 then uses the thumbnail camera 13 to obtain, as a dark-field thumbnail image, an image of the entirety of a glass slide GS in a dark-field state and stores data of the dark-field thumbnail image in a predetermined data format (the data may also be referred to as "dark-field thumbnail-image data" hereinafter).

Figure 3:
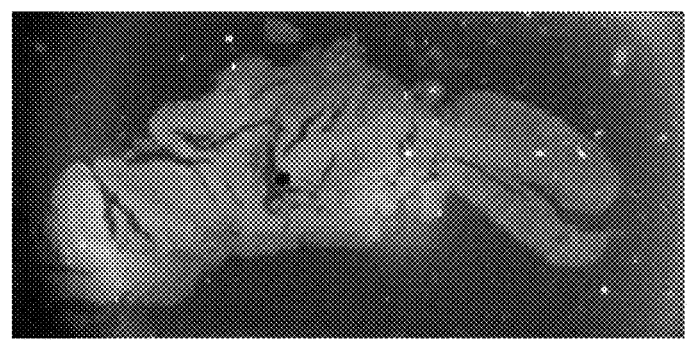
FIG. 3 is a pictorial representation of dark-field thumbnail image.

FIG. 3 shows one example of the dark-field thumbnail image when the tissue slice TS is stained by DAPI staining. As shown, the thumbnail-image capture unit 10 can capture a dark-field thumbnail image with which the profile shape of the DAPI-stained tissue slice TS can be roughly recognized.

The thumbnail-image capture unit 10 is configured so that the optical axis of the light emitted from the ultraviolet LED 12A is offset from the optical axis of the thumbnail camera 13 by a predetermined angle. With this arrangement, since the excitation light emitted from the ultraviolet LED 12A and reflection light resulting from reflection of the excitation light by the surface of the glass slide GS are not shined on the imaging surface of the thumbnail camera 13, the thumbnail-image capture unit 10 can prevent deterioration of the dark-field thumbnail image.

The magnified-image capture unit 20 captures a magnified image of the tissue slice TS after the moving stage 31 moves the glass slide GS to a magnified-image capture position EGP located between a bright-field filter 23 and an objective lens 24.

More specifically, in the magnified-image capture unit 20, in the case of the bright-field mode, after light emitted from a white-light source 21 is reflected by a reflection mirror 22, the resulting light is shined on the tissue slice TS from one side of the glass slide GS through the bright-field filter 23.

The magnified-image capture unit 20 magnifies an image of a tissue slice TS part, the image resulting from the light, to a predetermined scale by using the objective lens 24 and an image formation lens 25, which is provided at the other side of the glass slide GS. The magnified-image capture unit 20 focuses the image, magnified by the objective lens 24 and the image formation lens 25, on an imaging plane of an image-capture device 26.

The magnified-image capture unit 20 is adapted such that, in the case of the bright-field mode, a dichroic mirror 29 and an emission filter 30 can be removed from the optical path between the objective lens 24 and the image formation lens 25.

In the bright-field mode, the data processing unit 3 drives the white-light source 21, uses the image-capture device 26 to obtain a magnified image of the tissue slice TS in the bright-field state as a bright-field magnified image, and stores data of the bright-field magnified image in a predetermined data format (the data may also be referred to as "bright-field magnified-image data" hereinafter).

On the other hand, in the case of the dark-field mode, the magnified-image capture unit 20 causes an excitation-light source 27 to emit light and causes an excitation filter 28 to transmit, of the emitted light, only light having an excitation wavelength for the fluorescent stain. The excitation-light source 27 includes, for example, a mercury lamp.

The light transmitted through the excitation filter 28 (the light may hereinafter be referred to as "excitation light") is reflected by the dichroic mirror 29, which is provided between the objective lens 24 and the image formation lens 25, and then reaches the objective lens 24. In the magnified-image capture unit 20, the objective lens 24 then focuses the excitation light onto the tissue slice TS placed on the glass slide GS.

When the tissue slice TS is stained by fluorescent staining, the excitation light causes emission of the fluorescent stain and light (also referred to as "emission light" hereinafter) resulting from the emission passes through the dichroic mirror 29 via the objective lens 24. The emission light reaches the emission filter 30, which is provided between the dichroic mirror 29 and the image formation lens 25, and then reaches the image formation lens 25.

The magnified-image capture unit 20 magnifies an image resulting from the emission light by using the objective lens 24 and the image formation lens 25 and light (also referred to as "non-emission light" hereinafter) other than the emission light is absorbed by the emission filter 30. The magnified-image capture unit 20 is adapted to form, on the imaging plane of the image-capture device 26, an image of the emission light from which the non-emission light is eliminated.

In the dark-field mode, the data processing unit 3 drives the excitation-light source 27, uses the image-capture device 26 to obtain a magnified image of the tissue slice TS in the dark-field state as a dark-field magnified image, and stores data of the dark-field magnified image in a predetermined data format (the data may also be referred to as "dark-field magnified-image data" hereinafter).

[1-2. Configuration of Data Processing Unit]

Figure 4:
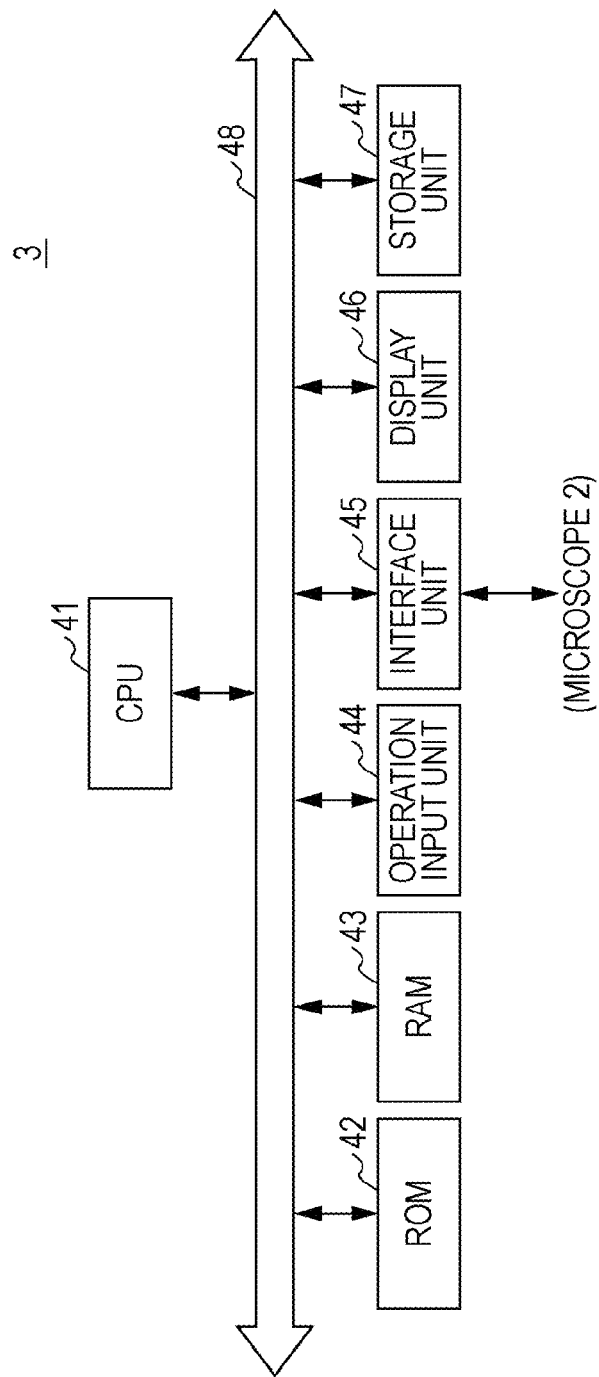
FIG. 4 is a block diagram illustrating the configuration of a data processing unit.

The configuration of the data processing unit 3 will be described next. As shown in FIG. 4, the data processing unit 3 has a configuration in which various types of hardware are connected to a CPU (central processing unit) 41 for performing control.

More specifically, a ROM (read only memory) 42, a RAM (random access memory) 43 serving as a work memory for the CPU 41, an operation input unit 44 for inputting an instruction corresponding to a user operation, an interface unit 45, a display unit 46, and a storage unit 47 are connected through a bus 48.

The ROM 42 stores programs for executing various types of processing. The microscope 2 (FIG. 1) is connected to the interface unit 45.

The display unit 46 may be implemented by a liquid crystal display, an EL (electroluminescent) display, a plasma display, or the like. The storage unit 47 may be implemented by a magnetic disk typified by a HD (hard disk), a semiconductor memory, an optical disk, or the like. The storage unit 47 may also be implemented by a portable memory, such as a USB (universal serial bus) memory, a CF (compact flash) memory, or the like.

The CPU 41 loads, of the programs stored in the ROM 42, the program associated with an instruction from the operation input unit 44 into the RAM 43. In accordance with the program loaded into the RAM 43, the CPU 41 controls the display unit 46 and the storage unit 47, as appropriate.

In accordance with the loaded program, the CPU 41 is also adapted to control the individual units of the microscope 2 via the interface unit 45, as appropriate.

[1-3. Details of Tissue-Slice Image Acquirement and Display Processing]

Upon receiving an instruction of acquirement and display of an image of the tissue slice TS from the operation input unit 44, the CPU 41 loads the program associated with the acquirement and display instruction into the RAM 43.

Figure 5:
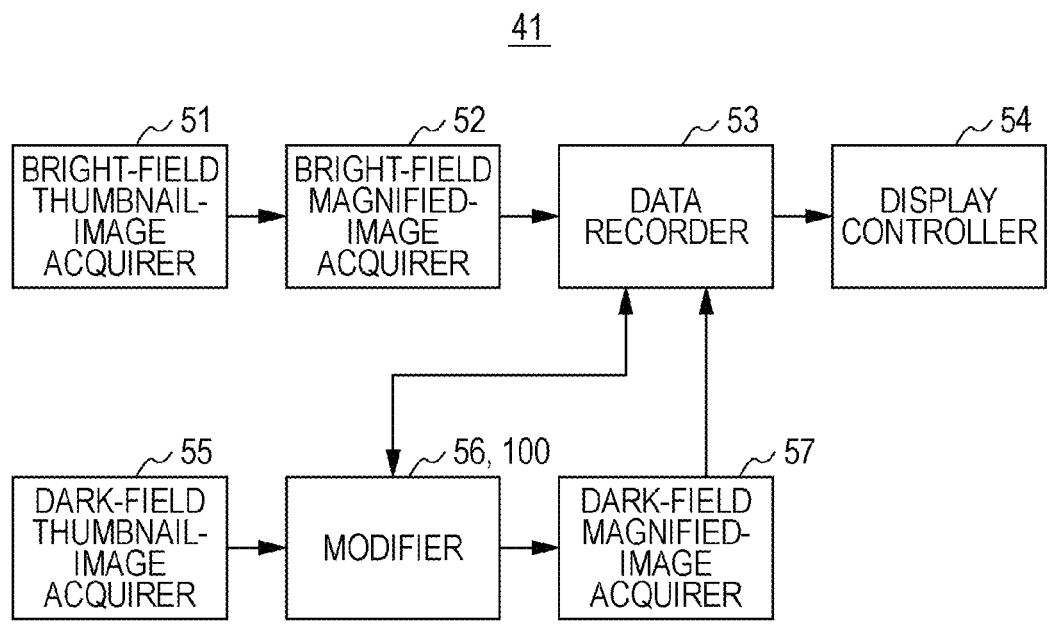
FIG. 5 is a block diagram showing the functional configuration of a CPU for executing a tissue-slice image acquirement and display processing.

As shown in FIG. 5, the CPU 41 serves as a bright-field thumbnail-image acquirer 51, a bright-field magnified-image acquirer 52, a data recorder 53, a display controller 54, a dark-field thumbnail-image acquirer 55, a modifier 56, and a dark-field magnified-image acquirer 57.

When the bright-field thumbnail-image acquirer 51 is to acquire an image of a tissue slice TS stained by HE staining used for a primary determination in the pathological diagnosis, the bright-field mode is selected in response to, for example, an operation of the operation input unit 44.

The bright-field thumbnail-image acquirer 51 causes the moving stage 31 to move so that a glass slide GS is located at the thumbnail-image capture position SGP and causes the white LED 11A in the bright-field light-source system 11 to be driven.

The bright-field thumbnail-image acquirer 51 uses the thumbnail camera 13 to capture an image of the entire glass slide GS including the tissue slice TS and acquires the image as a bright-field thumbnail image.

The bright-field magnified-image acquirer 52 causes the moving stage 31 to move so that the glass slide GS is located at the magnified-image capture position EGP.

The bright-field magnified-image acquirer 52 performs profile-shape extraction processing for extracting the profile shape of a tissue-slice portion from the bright-field thumbnail image acquired by the bright-field thumbnail-image acquirer 51. The profile-shape extraction processing involves, for example, processing for performing digitization processing for distinguishing between the tissue-slice portion and other regions and then extracting the profile shape of the digitized tissue-slice portion.

The bright-field magnified-image acquirer 52 detects a rectangular region having the smallest area encompassing the tissue-slice-portion profile shape extracted by the contour extraction processing.

Figure 6:
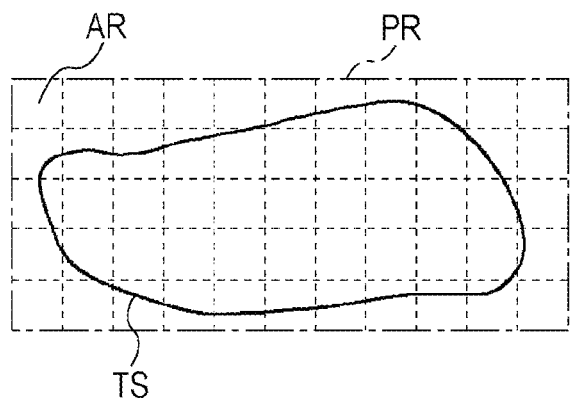
FIG. 6 is a schematic diagram showing assignment of image-capture range to a tissue slice.

By using relationships between pixel positions of the rectangular region in the bright-field thumbnail image and coordinate positions of the moving stage 31, the bright-field magnified-image acquirer 52 sets a rectangular image-capture range PR having the smallest area encompassing the tissue slice TS so as to correspond to the above-described rectangular region, as shown in FIG. 6.

The bright-field magnified-image acquirer 52 divides the image-capture range PR into multiple image-capture regions AR in accordance with magnifications of the objective lens 24 and the image formation lens 25 in the magnified-image capture unit 20 and an image-capture size of the image-capture device 26. Although the image-capture regions AR do not overlap with each other in the example of FIG. 6, adjacent regions may partially overlap with each.

The bright-field magnified-image acquirer 52 causes the white-light source 21 in the magnified-image capture unit 20 to be driven and causes the moving stage 31 to move sequentially so that a part whose image is to be captured by the image-capture device 26 corresponds to each of the image-capture regions AR.

The bright-field magnified-image acquirer 52 causes the image-capture device 26 to sequentially capture images of the individual parts of the tissue slice TS in the image-capture regions AR and combines the captured images of the individual parts to generate a bright-field magnified image.

The data recorder 53 records the bright-field thumbnail image, acquired by the bright-field thumbnail-image acquirer 51, and the bright-field magnified image, generated by the bright-field magnified-image acquirer 52, to the storage unit 47 in association with each other as bright-field thumbnail-image data and bright-field magnified-image data, respectively.

The data recorder 53 reads the relevant information from the barcode shown in the bright-field thumbnail image acquired by the bright-field thumbnail-image acquirer 51 and records the relevant information to the storage unit 47.

In this case, the data recorder 53 records the bright-field thumbnail-image data, the bright-field magnified-image data, and the relevant information in association with each other as a single data file.

When the relevant information is not obtained upon generation of the data file, the data recorder 53 is adapted to notify and alarm, at predetermined timing, that the relevant information is to be input.

When the predetermined data file is selected via the operation input unit 44, the display controller 54 reads the selected data file from the storage unit 47.

The display controller 54 causes the bright-field thumbnail image in the read data file to be displayed at an upper right portion on the display unit 46 and causes a bright-field magnified-image portion corresponding to an area where a cursor (for selecting a portion of the bright-field thumbnail image) is located to be displayed at a remaining portion on the display unit 46.

When a doctor or the like selects a region to be diagnosed from the bright-field thumbnail image by using the cursor, the display controller 54 is adapted to cause a bright-field magnified-image portion corresponding to the selected region to be displayed on the display unit 46 for primary diagnosis.

When the dark-field thumbnail-image acquirer 55 is to acquire an image of a tissue slice TS stained by fluorescent staining used for a secondary determination in the pathological diagnosis, the dark-field mode is selected in response to, for example, an operation of the operation input unit 44.

The relevant information of the barcode attached to a glass slide GS to which the fluorescence-stained tissue slice TS is fixed also includes a specimen number of an HE-stained tissue slice thinly cut from the same tissue block.

The dark-field thumbnail-image acquirer 55 causes the moving stage 31 to move so that the glass slide GS is located at the thumbnail-image capture position SGP and causes the ultraviolet LED 12A in the dark-field light-source system 12 to be driven.

The dark-field thumbnail-image acquirer 55 uses the thumbnail camera 13 to capture an image of the entire glass slide GS including the tissue slice TS and acquires the captured image as a dark-field thumbnail image. The dark-field thumbnail-image acquirer 55 reads the relevant information from the barcode attached to the glass slide GS.

Figure 7:
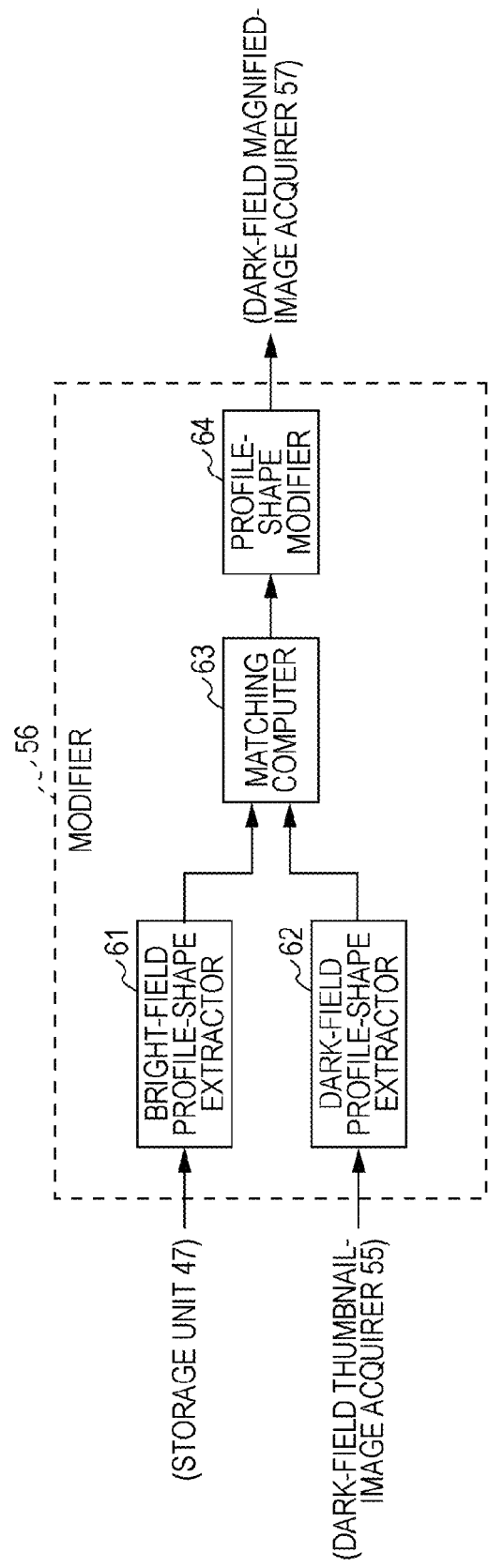
FIG. 7 is a block diagram showing the configuration of a modifier.

The modifier 56 modifies the profile shape of a tissue-slice portion in the dark-field thumbnail image. More specifically, as shown in FIG. 7, the modifier 56 serves as a bright-field profile-shape extractor 61, a dark-field profile-shape extractor 62, a matching computer 63, and a profile-shape modifier 64.

On the basis of the relevant information read by the dark-field thumbnail-image acquirer 55, the bright-field profile-shape extractor 61 reads a bright-field thumbnail image showing an image of the tissue slice TS thinly cut from the same tissue block as for the tissue slice TS shown in the dark-field thumbnail image.

The bright-field profile-shape extractor 61 digitizes the read bright-field thumbnail image by comparing, for example, luminance values of the pixels of the bright-field thumbnail image with a predetermined threshold set as a value that should be exhibited by the tissue-slice portion, to extract the region of the tissue-slice portion (the region may also be referred to as a "bright-field tissue-slice region").

Figure 8:
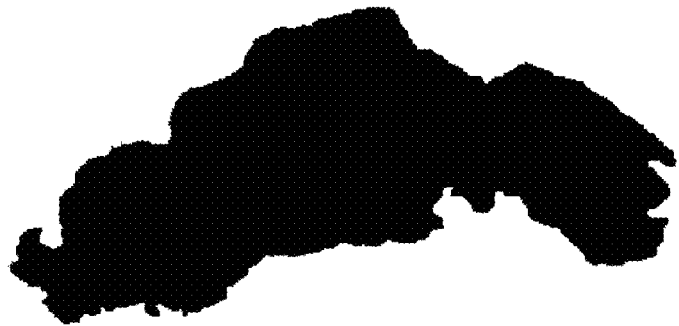
FIG. 8 is a pictorial representation of a bright-field tissue-slice region.

FIG. 8 illustrates one example of the bright-field tissue-slice region. As is clear from FIG. 8, the tissue-slice image acquirement and display apparatus 1 can capture an image of the tissue slice TS in a state in which it is sufficiently exposed in the bright-field mode, and thus can extract a bright-field tissue-slice region with which the profile shape of the tissue slice TS can be precisely recognized.

The dark-field profile-shape extractor 62 digitizes the dark-field thumbnail image, acquired by the dark-field thumbnail-image acquirer 55, by comparing luminance values of the pixels of the dark-field thumbnail image with a predetermined threshold set as a value that should be exhibited by the tissue-slice portion, to extract the region of the tissue-slice TS portion (the region may be referred to as a "dark-field tissue-slice region" hereinafter).

Figure 9:
FIG. 9 is a pictorial representation of a dark-field tissue-slice region.

FIG. 9 shows one example of the dark-field tissue-slice region. The bright-field tissue-slice region shown in FIG. 8 and the dark-field tissue-slice region shown in FIG. 9 are ones extracted from a bright-field thumbnail image and a dark-field thumbnail image obtained by capturing images of different tissue slices TS thinly cut from the same tissue block.

The tissue-slice image acquirement and display apparatus 1 may not be able to capture an image of a tissue slice TS with sufficient brightness in the dark-field mode, and the influence of disturbance, such as electrical and optical noise, may cause deterioration of a dark-field thumbnail image. In such a case, the profile (contour) of the tissue slice TS in the dark-field thumbnail image is blurred.

Consequently, the dark-field tissue-slice region extracted by the dark-field profile-shape extractor 62 varies depending on the setting of the threshold. Residues left after rising of the fluorescent stain used for fluorescent staining, dust attached to the glass slide GS, and so on are also extracted into the dark-field tissue-slice region.

Thus, with the tissue-slice image acquirement and display apparatus 1, it is difficult to extract a dark-field tissue-slice region with which the profile shape of the tissue slice TS can be precisely recognized.

Since the HE-stained tissue slice TS and the fluorescence-stained tissue slice TS are thinly cut from the same tissue block and are fixed to the separate glass slides GS, the positions on the glass slides GS may be displaced from each other and the obverse and reverse sides thereof may be opposite to each other.

The matching computer 63 determines the amount of displacement between the bright-field tissue-slice region extracted by the bright-field profile-shape extractor 61 and the dark-field tissue-slice region extracted by the dark-field profile-shape extractor 62.

Specifically, for example, the matching computer 63 determines a barycenter position of the bright-field tissue-slice region and a barycenter position of the dark-field tissue-slice region and determines the difference between the barycenter positions as the amount of positional displacement.

The matching computer 63 moves the bright-field tissue-slice region by an amount corresponding to the amount of positional displacement so that the barycenter of the bright-field tissue-slice region and the barycenter of the dark-field tissue-slice region match each other. The matching computer 63 determines mean square differences by obtaining differences between the bright-field tissue-slice region and the dark-field tissue-slice region, while shifting the moved bright-field tissue-slice region about the barycenter thereof by a predetermined angle.

The matching computer 63 obtains, as an amount of angular displacement, an angle at which the mean square difference is the smallest, i.e., an angle at which the correlation is the highest. Consequently, matching computer 63 obtains the amount of angular displacement and the above-described amount of positional displacement.

Since the tissue slices TS thinly cut from the same tissue block are shown in the bright-field thumbnail image and the dark-field thumbnail image, they have substantially the same profile shape.

Thus, the profile-shape modifier 64 moves the bright-field tissue-slice region in the bright-field thumbnail image by an amount corresponding to the amounts of displacement determined by the matching computer 63, i.e., the amount of positional displacement and the amount of angular displacement.

The position and the profile shape of the bright-field tissue-slice region moved by an amount corresponding to the amounts of displacement represent the position and the profile shape of the tissue-slice portion in the dark-field thumbnail image. The profile-shape modifier 64 generates profile information indicating the position and the profile shape of the bright-field tissue-slice region moved by an amount corresponding to the amounts of displacement.

The profile-shape modifier 64 modifies the profile shape of the tissue-slice portion in the dark-field thumbnail image by replacing the profile shape of the tissue-slice portion in the dark-field thumbnail image with the profile shape of the bright-field tissue-slice region indicated by the generated profile information.

The dark-field magnified-image acquirer 57 causes the moving stage 31 to move so that the glass slide GS is located at the magnified-image capture position EGP.

The dark-field magnified-image acquire 57 uses the profile information generated by the profile-shape modifier 64 to set a rectangular shape including the tissue slice TS as the image-capture range PR.

The dark-field magnified-image acquirer 57 divides the image-capture range PR into multiple image-capture regions AR in accordance with magnifications of the objective lens 24 and the image formation lens 25 in the magnified-image capture unit 20 and an image-capture size of the image-capture device 26.

The dark-field magnified-image acquirer 57 causes the excitation-light source 27 in the magnified-image capture unit 20 to be driven and causes the moving stage 31 to move sequentially so that a part whose image is to be captured by the image-capture device 26 corresponds to each of the image-capture regions AR. The dark-field magnified-image acquirer 57 causes the image-capture device 26 to sequentially capture images of the individual parts of the tissue slice TS in the image-capture regions AR and combines the captured images of the individual parts to generate a dark-field magnified image.

The data recorder 53 records the dark-field thumbnail image, acquired by the dark-field thumbnail-image acquirer 55, to the storage unit 47 as dark-field thumbnail-image data. The data recorder 53 also records the amounts of displacement determined by the modifier 56 and the dark-field magnified image acquired by the dark-field magnified-image acquirer 57 to the storage unit 47 as displacement-amount information and dark-field magnified-image data, respectively.

In this case, the data recorder 53 records the dark-field thumbnail-image data, the displacement-amount information, and the dark-field magnified-image data to a corresponding data file in conjunction with the bright-field thumbnail-image data, the bright-field magnified-image data, and the relevant information.

When the predetermined data file is selected via the operation input unit 44 and an instruction for displaying the dark-field magnified image is executed, the display controller 54 reads the selected data file from the storage unit 47. On the basis of the displacement-amount information, the display controller 54 determines pixels of the dark-field magnified image which correspond to pixels of the bright-field thumbnail image.

Figure 10:
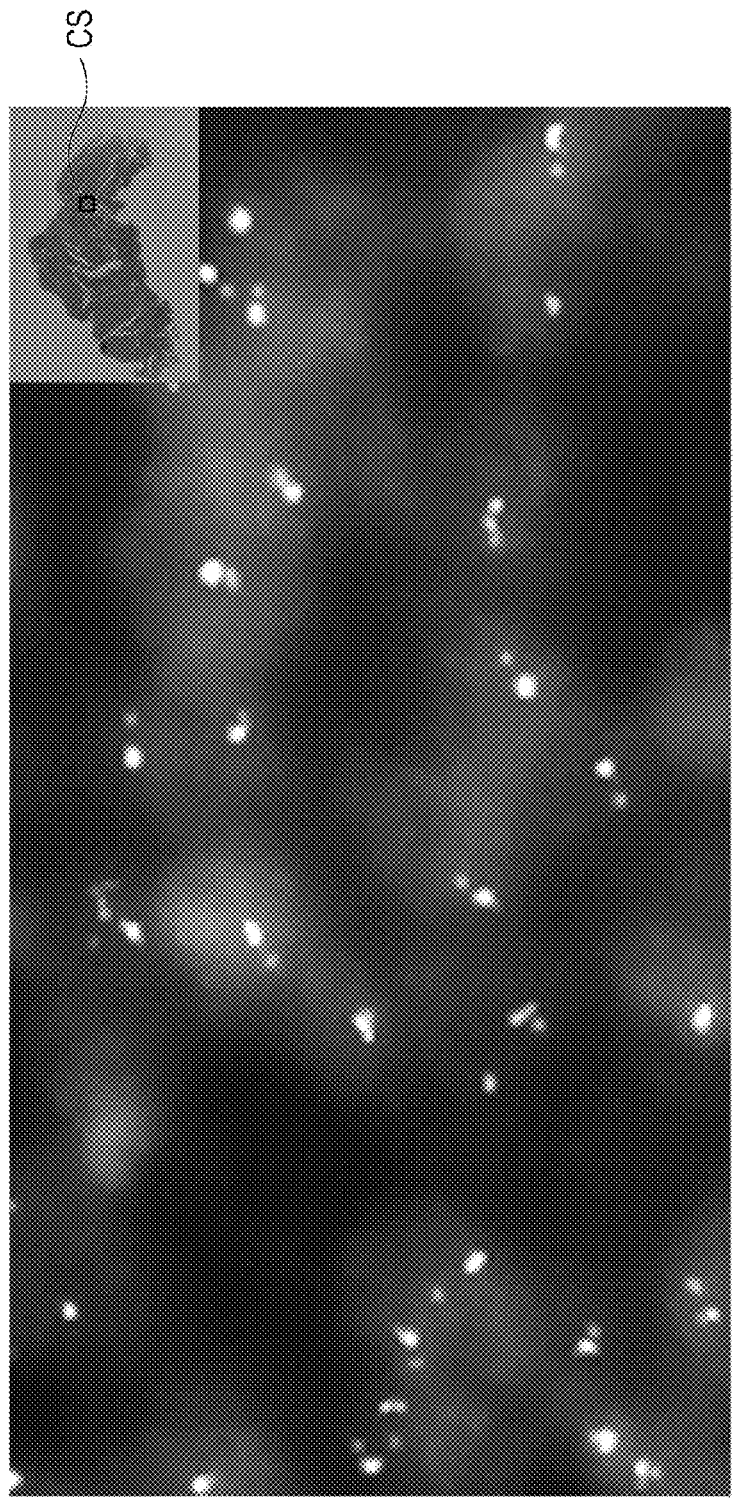
FIG. 10 shows a dark-field magnified-image display screen.

As shown in FIG. 10, the display controller 54 displays, on the display unit 46, a dark-field magnified-image screen G1 showing the bright-field thumbnail image at an upper right portion thereof and showing the dark-field magnified image of a portion selected with the cursor CS for selecting a portion of the bright-field thumbnail image.

Thus, when a doctor or the like selects a region to be diagnosed in the bright-field thumbnail image used in the primary diagnosis by using the cursor CS, the display controller 54 is adapted to cause a dark-field magnified-image portion corresponding to the selected portion to be displayed on the display unit 46 for secondary diagnosis.

[1-4. Tissue-Slice Acquirement and Display Processing Procedure]

Figure 11:
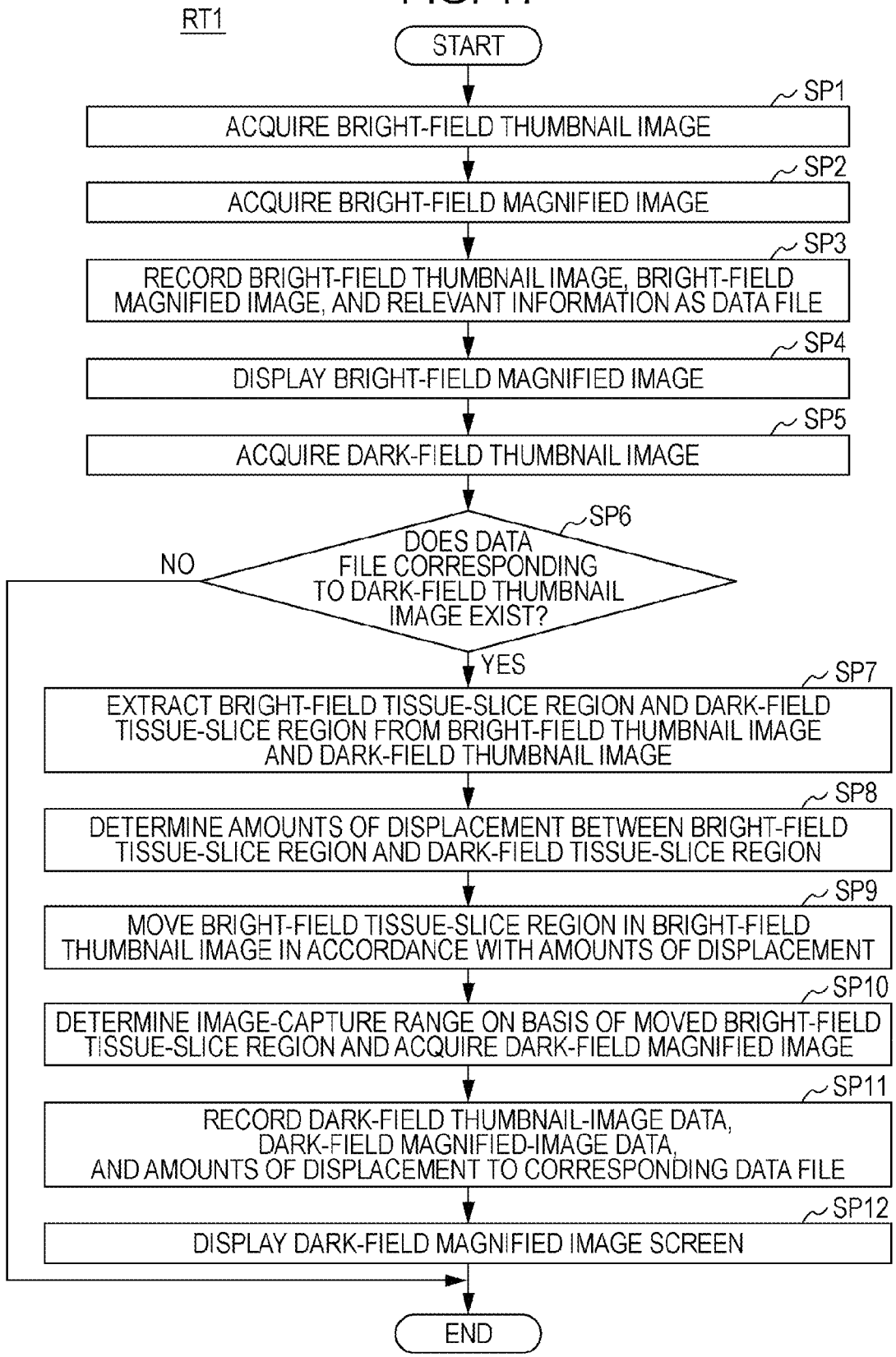
FIG. 11 is a flowchart of a tissue-slice acquirement and display processing procedure.

A procedure for the tissue-slice acquirement and display processing will now be described with reference to a flowchart shown in FIG. 11.

In practice, the CPU 41 proceeds to step SP1 after entering a "start" step in routine RT1. In step SP1, the CPU 41 uses the thumbnail camera 13 to capture an image of an entire glass slide GS including a tissue slice TS and acquires the captured image as a bright-field thumbnail image. The process then proceeds to step SP2.

In step SP2, the CPU 41 divides an image-capture range PR corresponding to a range including a tissue-slice portion in the bright-field thumbnail image into multiple image-capture regions AR. The CPU 41 causes the image-capture device 26 to sequentially capture images of individual parts of the tissue slice TS which correspond to the image-capture regions AR and combines the captured images to generate a bright-field magnified image. The process then proceeds to step SP3.

In step SP3, the CPU 41 records bright-field thumbnail-image data, bright-field magnified-image data, and relevant information in association with each other as a single data file. The process then proceeds to step SP4.

In step SP4, the CPU 41 causes the bright-field thumbnail image to be displayed at an upper right portion on the display unit 46 and causes the bright-field magnified image of a portion corresponding to the cursor CS (for selecting a portion of the bright-field thumbnail image) to be displayed at a remaining portion on the display unit 46. The process then proceeds to step SP5.

In step SP5, the CPU 41 uses the thumbnail camera 13 to capture an image of an entire glass slide GS including a fluorescence-stained tissue slice TS and acquires the captured image as a dark-field thumbnail image. The process then proceeds to step SP6.

In step SP6, on the basis of the relevant information of the barcode attached to the glass slide GS to which the tissue slice TS is fixed, the CPU 41 determines whether or not a data file corresponding to the dark-field thumbnail image obtained in step SP5 exists.

When a negative result (i.e., NO) is obtained in step SP6, this means that a bright-field thumbnail image of a tissue slice TS thinly cut from the same tissue block as for the fluorescence-stained tissue slice TS shown in the dark-field thumbnail image and subjected to HE staining does not exist. In this case, the CPU 41 proceeds to a next step to end the processing.

On the other hand, when an affirmative result (i.e., YES) is obtained in step SP6, this means that a bright-field thumbnail image of a tissue slice TS thinly cut from the same tissue block as for the fluorescence-stained tissue slice TS shown in the dark-field thumbnail image and subjected to HE staining exists. In this case, the CPU 41 proceeds to step SP7.

In step SP7, the CPU 41 reads the bright-field thumbnail-image data from the data file and extracts a bright-field tissue-slice region and a dark-field tissue-slice region on the basis of thresholds respectively set for the bright-field thumbnail image and the dark-field thumbnail image. The process then proceeds to step SP8.

In step SP8, the CPU 41 determines an amount of angular displacement and an amount of positional displacement between the bright-field tissue-slice region and the dark-field tissue-slice region. The process then proceeds to step SP9

In step SP9, the CPU 41 moves the bright-field tissue-slice region in the bright-field thumbnail image by an amount corresponding to the amounts of displacement, i.e., the amount of positional displacement and the amount of angular displacement. The process then proceeds to step SP10.

In step SP10, on the basis of the profile shape of the moved bright-field tissue-slice region, the CPU 41 sets, as the image-capture range PR, a rectangular range having the smallest area encompassing the tissue slice TS whose image is to be captured in the dark-field mode.

The CPU 41 divides the image-capture range PR into multiple image-capture regions AR, causes the image-capture device 26 to sequentially capture images of individual parts of the tissue slice TS which correspond to the image-capture regions AR and combines the captured images to generate a dark-field magnified image. The process then proceeds to step SP11.

In step SP11, the CPU 41 records the dark-field thumbnail-image data, the dark-field magnified-image data, and the amounts of displacement to a corresponding data file. The process then proceeds to step SP12.

In step SP12, the CPU 41 reads the data file from the storage unit 47 and displays the dark-field magnified image screen G1 on the display unit 46. The process then proceeds to a next step to thereby end the processing.

[1-5. Operation and Advantages]

In the configuration described above, the tissue-slice image acquirement and display apparatus 1 acquires, as a bright-field thumbnail mage, an image of an entire tissue slice TS subjected to staining to be used for image capture in a bright-field state, and also acquires, as a dark-field thumbnail image, an image of an entire tissue slice TS subjected to fluorescent staining, both the tissue slices TS being thinly cut from the same tissue block.

The tissue-slice image acquirement and display apparatus 1 compares the individual pixels of the bright-field thumbnail image and the individual pixels of the dark-field thumbnail image with corresponding preset thresholds to extract tissue-slice portions as a bright-field tissue-slice region and a dark-field tissue-slice region.

The tissue-slice image acquirement and display apparatus 1 determines, as the amounts of displacement, the amount of positional displacement and the amount of angular displacement between the bright-field tissue-slice region and the dark-field tissue-slice region and then moves the bright-field tissue-slice region in the bright-field thumbnail image on the basis of the amounts of displacement.

By using the profile shape of the moved bright-field tissue-slice region as the profile shape of the tissue-slice portion in the dark-field thumbnail image, the tissue-slice image acquirement and display apparatus 1 obtains a dark-field magnified image in the image-capture range PR corresponding to a range encompassing the profile shape of the tissue-slice portion.

The tissue-slice image acquirement and display apparatus 1 displays, on the display unit 46, the dark-field magnified-image screen G1 showing the bright-field thumbnail image at an upper right portion thereof and showing the dark-field magnified image of a portion selected with the cursor CS for selecting a portion of the bright-field thumbnail image.

With this arrangement, when a portion of the bright-field thumbnail image observed in the primary diagnosis is selected with the cursor CS, the tissue-slice image acquirement and display apparatus 1 displays, on the display unit 46, a dark-field magnified image corresponding to the selected portion. Thus, with the tissue-slice image acquisition and display apparatus 1, the user does not have to search for, in the dark-field thumbnail image, a region corresponding to a part diagnosed as suspicious in the primary diagnosis. Correspondingly, user convenience can be improved.

During extraction of a dark-field tissue-slice region when a dark-field thumbnail image with sufficient brightness is not captured in the dark-field mode, an event in which a tissue-slice portion that is smaller than the actual tissue-slice portion is extracted may occur. In such an event, when a dark-field magnified image is captured based on the profile shape of the dark-field tissue-slice region, the tissue slice TS in the dark-field magnified image is partly lost.

It is also conceivable that a tissue-slice portion that is larger than the actual tissue-slice portion is detected from the dark-field thumbnail image as the dark-field tissue-slice region. In such a case, however, since a magnified image of an excessive portion is obtained, the amount of data increases.

In contrast, according to the tissue-slice image acquirement and display apparatus 1, even when a tissue-slice portion that is smaller than the actual tissue-slice portion is extracted as the dark-field tissue-slice portion, the dark-field magnified image is obtained on the basis of the profile shape of the bright-field tissue-slice region in the bright-field thumbnail image.

Thus, since the tissue-slice image acquirement and display apparatus 1 acquires the dark-field magnified image by using the profile shape of the bright-field tissue-slice region into which the profile shape of the tissue slice TS in the bright-field thumbnail image is precisely extracted, it is possible to prevent partial loss of the tissue slice TS in the dark-field magnified image. Thus, the tissue-slice image acquirement and display apparatus 1 can acquire a dark-field magnified image with precision and with the entire tissue slice TS being included in its image capture range without excess or insufficiency.

According to the above-described configuration, the profile shape of the tissue-slice portion in the dark-field thumbnail image is modified on the basis of the bright-field thumbnail image, the modified profile shape is used to obtain a dark-field magnified image, and both of the bright-field thumbnail image and the dark-field magnified image are displayed.

With this arrangement, the tissue-slice image acquirement and display apparatus 1 can accurately obtain the profile shape of the tissue-slice portion in a bright-field thumbnail image and also can acquire a dark-field magnified image with precision while enhancing convenience.

2. Other Embodiments

In the above-described embodiment, the amounts of displacement between the bright-field tissue-slice region and the dark-field tissue-slice region are determined and the bright-field tissue-slice region in the bright-field thumbnail image is moved by an amount corresponding to the amounts of displacement. The profile shape of the tissue-slice portion in the dark-field thumbnail image is then replaced with the profile shape of the moved bright-field tissue-slice region to thereby modify the profile shape of the tissue-slice portion in the dark-field thumbnail image.

The present application, however, is not limited to this arrangement. For example, the dark-field tissue-slice region may be extracted from the dark-field thumbnail image so that the area of the dark-field tissue-slice region becomes equal to the area of the bright-field tissue-slice region, to thereby modify the profile shape of the tissue-slice portion in the dark-field thumbnail image.

Figure 12:
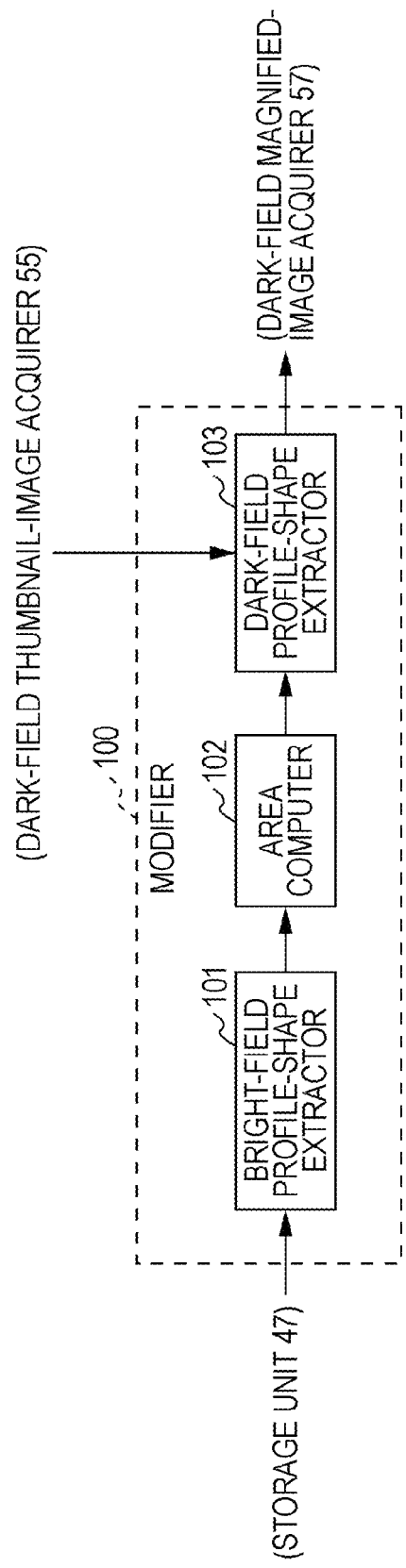
FIG. 12 is a block diagram showing the configuration of a modifier in another embodiment.

More specifically, the CPU 41 in the tissue-slice image acquirement and display apparatus 1 provides a modifier 100 (in FIG. 5) instead of the modifier 56 in the above-described embodiment. As shown in FIG. 12, the modifier 100 serves as a bright-field profile-shape extractor 101, an area computer 102, and a dark-field profile-shape extractor 103.

On the basis of the relevant information read by the dark-field thumbnail-image acquirer 55, the bright-field profile-shape extractor 101 reads a bright-field thumbnail image showing an image of a tissue slice TS thinly cut from the same tissue block as for the tissue slice TS shown in the dark-field thumbnail image.

The bright-field profile-shape extractor 101 compares luminance values of the pixels of the read bright-field thumbnail image with a predetermined threshold set as a value that should be exhibited by the tissue slice, to extract the bright-field tissue-slice region.

The area computer 102 computes the area of the bright-field tissue-slice region extracted by the bright-field profile-shape extractor 101. The area computer 102 may determine the number of pixels in the bright-field tissue-slice region as the area thereof or may determine an actual area based on the image-capture magnification of the thumbnail camera 13.

The dark-field profile-shape extractor 103 extracts a dark-field tissue-slice region by comparing luminance values of the pixels of the dark-field thumbnail image with a predetermined threshold and determines the area of the dark-field tissue-slice region.

When the determined area of the dark-field tissue-slice region is not in a range that can be regarded as being equal to the bright-field tissue-slice region area determined by the area computer 102, the dark-field profile-shape extractor 103 changes the threshold The dark-field profile-shape extractor 103 then uses the changed threshold to extract a dark-field tissue-slice region again, determines the area thereof, and compares the area with the area of the bright-field tissue-slice region. The dark-field profile-shape extractor 103 changes the threshold until the area of the dark-field tissue-slice region is in the range that can be regarded as being equal to the area of the bright-field tissue-slice region, to extract the dark-field tissue-slice region.

When the area of the dark-field tissue-slice region is in the range that can be regarded as being equal to the area of the bright-field tissue-slice region, the dark-field profile-shape extractor 103 obtains the profile shape of the dark-field tissue-slice region as the profile information.

As described above, the modifier 100 changes the threshold so that the area of the dark-field tissue-slice region becomes equal to the area of the bright-field tissue-slice region to extract the dark-field tissue-slice region. Thus, even when the profile (contour) of the tissue slice TS is blurred because of a small amount of light in the dark-field mode, the modifier 100 can extract the dark-field tissue-slice region so that the area of the dark-field tissue slice region becomes equal to the area of the tissue slice TS image captured in the bright-field mode. This makes it possible to extract a dark-field tissue-slice region that more precisely indicates the profile shape of the tissue slice TS Even when the area of the dark-field tissue-slice region becomes equal to the area of the bright-field tissue-slice region, the profile of the dark-field tissue-slice region may have a recessed portion in some cases. In such cases, a tissue slice TS portion corresponding to the recessed portion may be uncaptured as a dark-field magnified image.

Accordingly, the dark-field profile-shape extractor 103 may change the threshold so that the area of the dark-field tissue-slice region and the area of the bright-field tissue-slice region become equal to each other and the area of a polygon having the smallest area encompassing the dark-field tissue-slice region and the area of a polygon having the smallest area encompassing the bright-field tissue-slice region become equal to each other, to extract the dark-field tissue-slice region.

Wit this arrangement, even when the profile of the dark-field tissue-slice region has a recessed portion, the modifier 100 can prevent a tissue slice TS portion corresponding to the recessed portion from becoming uncaptured as the dark-field magnified image, by making the area of the polygon encompassing the dark-field tissue-slice region become equal to the area of the polygon encompassing the bright-field tissue-slice region.

In the above-described embodiment, the bright-field tissue-slice region and the dark-field tissue-slice region are extracted on the basis of the luminance values of the bright-field thumbnail image and the dark-field thumbnail image, respectively. The present application is not limited to this arrangement. For example, the bright-field tissue-slice region and the dark-field tissue-slice region may be extracted on the basis of color information of the bright-field thumbnail image and the dark-field thumbnail image, respectively.

Although the description in the above embodiment has been given of a case in which digitization is performed by comparing the luminance values of the pixels of the dark-field thumbnail image with the threshold set as a value that should be exhibited by the tissue slice portion and the dark-field tissue-slice region is extracted, the present application is not limited thereto. For example, the arrangement may also be such that digitization is performed by comparing the luminance values of the pixels of the dark-field thumbnail image with the threshold set as a value that should be exhibited by the tissue slice portion and a single largest region of extracted regions is extracted as the dark-field tissue-slice region.

In such a case, residues left after rinsing of the fluorescent stain used for the fluorescent staining, dust attached to the glass slide GS, and so on can be removed from a dark-field tissue-slice region as shown in FIG. 9.

In the above-described embodiment, after determining the amount of positional displacement through determination of the barycenter positions of the bright-field tissue-slice region and the dark-field tissue-slice region, the tissue-slice image acquirement and display apparatus 1 determines mean square differences by obtaining differences between the pixels while shifting the angle of the bright-field tissue-slice region by a predetermined angle, to determine the amount of angular displacement. The present application is not limited to this arrangement. For example, the tissue-slice image acquirement and display apparatus 1 may determine mean square differences by obtaining differences between the pixels while shifting the position and the angle of one of the bright-field tissue-slice region and the dark-field tissue-slice region, to determine the amount of positional displacement and the amount of angular displacement.

Although a case in which DAPI is used as a fluorescent stain has been described in the above embodiment, the present application is not limited thereto. That is, any fluorescent stain that allows for recognition of the profile shape of the tissue slice TS may be used.

In addition, although a case in which the CPU 41 performs the above-described biometric-sample-image acquirement processing in accordance with a program stored in the ROM 42 has been described in the above embodiment, the present application is not limited thereto. For example, the above-described biometric-sample-image acquirement processing may be executed in accordance with a program installed from a storage medium or downloaded over the Internet. The above-described biometric-sample-image acquirement processing may be performed in accordance with a program installed through any other channel.

The description in the above embodiment has been given of a case in which the bright-field thumbnail-image acquirer 51 and the dark-field thumbnail-image acquirer 55 serving as an entire-image acquirer, the modifier 56, the thumbnail camera 13 serving as a magnified-image acquirer, and the display controller 54 are provided. According to the present application, however, a light source and an image capture unit having any other configurations may also be provided.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A tissue-slice image acquirement and display apparatus comprising:
    an entire-image acquirer configured to:
    acquire a bright-field image of an entirety of a first slice of a tissue; and
    acquire a dark-field image of an entirety of a second slice of the tissue;
    a modifier configured to:
    extract a bright-field profile shape of the first slice portion within the bright-field image;
    extract a dark-field profile shape of the second slice portion within the dark-field image;
    modify the dark-field profile shape by:
    aligning positionally the bright-field image with the dark-field image, and
    replacing the dark-field profile shape of the second slice portion with the bright-field profile shape of the first slice portion for the dark-field image;
    a magnified-image acquirer configured to determine a range encompassing the second slice on a basis of the dark-field profile shape modified by the modifier and that acquires, in a dark field, a magnified image of the second slice in the determined range; and
    a display controller configured to cause the bright-field image to be displayed and cause a portion of the magnified image, the portion corresponding to a position selected in the bright-field image, to be displayed.

2. The apparatus according to claim 1, wherein the modifier modifies the dark-field profile shape by replacing the dark-field profile shape of the slice portion in the dark-field image with the bright-field profile shape responsive to detecting that the dark-field profile shape has a smaller area than the bright-field profile shape.

3. The apparatus according to claim 1, wherein the modifier modifies dark-field profile shape so that an area of the dark-field profile shape becomes equal to an area of the bright-field profile shape.

4. The apparatus according to claim 1, wherein the modifier modifies the dark-field profile shape so that an area of the bright-field profile shape and an area of the dark-field profile shape become equal to each other and an area of a polygon having a smallest area encompassing the bright-field profile shape and an area of a polygon having a smallest area encompassing the dark-field profile shape become equal to each other.

5. The apparatus according to claim 1, wherein the modifier aligns the dark-field profile shape with the bright-field profile shape by:
    determining a first barycenter position of the bright-field profile shape;
    determining a second barycenter position of the dark-field profile shape;
    determining a positional displacement based on a difference between the first and second barycenter positions; and
    shifting the dark-field profile shape by the positional displacement so that the first barycenter position substantially matches the second barycenter position.

6. The apparatus according to claim 5, wherein the modifier aligns the dark-field profile shape with the bright-field profile shape by determining an angular displacement between the dark-field profile shape and the bright-field profile shape by determining a smallest mean square difference between the bright-field profile shape and shifted versions of the dark-field profile shape that are rotated around the second barycenter position.

7. The apparatus according to claim 6, wherein the display controller causes the bright-field image and the portion of the magnified image to be displayed by determining pixels of the magnified image that correspond to pixels of the position selected in the bright-field image based on at least one of the of positional displacement or the angular displacement.

8. The apparatus according to claim 1, wherein the bright-field image is stored as a first thumbnail image and the dark-field image is stored as a second thumbnail image.

9. The apparatus according to claim 1, wherein the entire-image acquirer is configured to be offset by a predetermined angle from an optical axis of a light source.

10. A tissue-slice image acquirement and display method comprising:
    acquiring a bright-field image, via a processor, of an entirety of a first slice of a tissue and a dark-field image of an entirety of a second slice of the tissue;
    determining, via the processor, a bright-field profile shape of the first slice portion within the bright-field image;
    determining, via the processor, a dark-field profile shape of the second slice portion within the dark-field image;
    modifying, via the processor, the dark-field profile shape by:
    aligning positionally the bright-field image with the dark-field image, and
    replacing the dark-field profile shape of the second slice portion with the bright-field profile shape of the first slice portion for the dark-field image;
    determining, via the processor, a range encompassing the second slice on a basis of the dark-field profile shape as modified and acquiring, in a dark field, a magnified image of the second slice in the determined range; and causing, via the processor, the bright-field image to be displayed by a display unit and causing a portion of the magnified image, the portion corresponding to a position selected in the bright-field image, to be displayed.

11. A tissue-slice image acquirement and display program causing a computer to execute the steps of:

acquiring a bright-field image of an entirety of a first slice of a tissue and a dark-field image of an entirety of a second slice of the tissue;

determining a bright-field profile shape of the first slice portion within the bright-field image;

determining a dark-field profile shape of the second slice portion within the dark-field image;

modifying the dark-field profile shape by:
aligning positionally the bright-field image with the dark-field image, and
replacing the dark-field profile shape of the second slice portion with the bright-field profile shape of the first slice portion for the dark-field image;

determining a range encompassing the second slice on a basis of the dark-field profile shape as modified and acquiring, in a dark field, a magnified image of the second slice in the determined range; and causing the bright-field image to be displayed and causing a portion of the magnified image, the portion corresponding to a position selected in the bright-field image, to be displayed.

* * * * *